US008809766B2

(12) United States Patent
Ma

(10) Patent No.: US 8,809,766 B2
(45) Date of Patent: Aug. 19, 2014

(54) METHODS AND SYSTEMS FOR DETECTING OR COLLECTING PARTICLES

(75) Inventor: Yuchen Ma, Shanghai (CN)

(73) Assignee: Empire Technology Development LLC, Wilmington, DE (US)

( * ) Notice: Subject to any disclaimer, the term of this patent is extended or adjusted under 35 U.S.C. 154(b) by 41 days.

(21) Appl. No.: 13/807,148

(22) PCT Filed: Jun. 28, 2011

(86) PCT No.: PCT/CN2011/076488
§ 371 (c)(1),
(2), (4) Date: May 30, 2013

(87) PCT Pub. No.: WO2012/000424
PCT Pub. Date: Jan. 5, 2012

(65) Prior Publication Data
US 2013/0240752 A1    Sep. 19, 2013

(30) Foreign Application Priority Data

Jun. 29, 2010    (CN) .......................... 2010 1 0214848

(51) Int. Cl.
G01N 15/10    (2006.01)
A01N 25/28    (2006.01)
H01L 31/0352  (2006.01)
(52) U.S. Cl.
USPC ........... 250/251; 250/325; 250/397; 324/464; 324/463; 264/10

(58) Field of Classification Search
CPC ............... B01D 7/02; B01D 2239/025; B01D 2239/0258; B01D 2323/40; B01D 67/0088; B01D 69/125; B01D 69/148; B01D 71/82; A01N 25/28; H01L 31/0352
USPC .................. 250/251, 397, 325; 324/464, 463; 264/10
See application file for complete search history.

(56) References Cited

U.S. PATENT DOCUMENTS

| 2,490,979 A | 12/1949 | Palmer |
| 3,449,093 A | 6/1969 | Baxt et al. |
| 4,185,972 A | 1/1980 | Nitta et al. |
| 4,257,258 A | 3/1981 | Bovenlander |
| 4,308,223 A | 12/1981 | Stern |
| 4,564,721 A | 1/1986 | Ishikawa et al. |

(Continued)

FOREIGN PATENT DOCUMENTS

| CN | 1869648 | 11/2006 |
| CN | 101526460 | 9/2009 |

(Continued)

OTHER PUBLICATIONS

International Search Report and Written Opinion for PCT/CN2011/076488 dated Oct. 20, 2011.

(Continued)

Primary Examiner — Nikita Wells
(74) Attorney, Agent, or Firm — Foley & Lardner LLP

(57) ABSTRACT

Methods and systems for detecting and/or collecting particles are disclosed. At least some of the particles are electrically charged by a charger (122). At least some of the charged particles are collected by a collector (140). Information indicating the number of the detected/collected particles based on measured electrical charges of the charged particles is obtained by a processor (170).

18 Claims, 11 Drawing Sheets

(56) References Cited

U.S. PATENT DOCUMENTS

| | | | |
|---|---|---|---|
| 4,874,399 | A | 10/1989 | Reed et al. |
| 5,474,600 | A | 12/1995 | Volodina et al. |
| 5,549,735 | A | 8/1996 | Coppom |
| 5,578,113 | A | 11/1996 | Glenn |
| 5,639,287 | A | 6/1997 | Van de Graaf et al. |
| 5,766,318 | A | 6/1998 | Loreth et al. |
| 6,225,623 | B1 | 5/2001 | Turner et al. |
| 6,527,834 | B1 | 3/2003 | Jorder et al. |
| 6,573,205 | B1 | 6/2003 | Myers et al. |
| 6,616,736 | B2 | 9/2003 | Massey et al. |
| 6,749,669 | B1 | 6/2004 | Griffiths et al. |
| 6,888,140 | B2 | 5/2005 | Hayn |
| 7,041,925 | B2 | 5/2006 | Gates |
| 7,101,422 | B1 | 9/2006 | Altman et al. |
| 7,262,384 | B2 * | 8/2007 | Jackson .................... 219/121.43 |
| 7,294,169 | B2 | 11/2007 | Taylor |
| 7,680,243 | B2 | 3/2010 | Yokhin et al. |
| 7,728,253 | B2 | 6/2010 | Hopwood |
| 7,736,553 | B2 * | 6/2010 | Halpap et al. .................... 264/10 |
| 8,658,056 | B1 * | 2/2014 | Cook et al. ............... 252/299.01 |
| 2006/0180023 | A1 | 8/2006 | Coppom et al. |
| 2007/0028767 | A1 | 2/2007 | Choi et al. |
| 2013/0001833 | A1 * | 1/2013 | Niedermeyer ................ 264/400 |

FOREIGN PATENT DOCUMENTS

| | | |
|---|---|---|
| CN | 101887003 | 11/2010 |
| EP | 0 620 044 | 10/1994 |
| GB | 2 308 320 | 6/1997 |
| JP | 62-043540 | 2/1987 |
| JP | 63-178864 | 7/1988 |
| JP | 01-258714 | 10/1989 |
| JP | 06-218211 | 8/1994 |
| JP | 2006-194882 | 7/2006 |
| JP | 2008-536136 | 9/2008 |
| WO | WO-2009/109688 | 9/2009 |

OTHER PUBLICATIONS

Baumgartner, H and Loffler, F., "Particle Collection in Electret Fibrous Filters: A Basic Theoretical and Experimental Study," Filtration and separation, vol. 24, No. 5, pp. 346-351 (1987).

International Preliminary Report on Patentability in PCT/CN2011/076488 dated Jan. 8, 2011, pp. 1-7.

International Search Report for PCT/CN2011/078747 Dated May 31, 2012.

J. Van Turnhout, J.W.C. Adamse and W.J. Hoeneveld, "Electret filters for high-efficiency air cleaning," Journal of Electrostatics vol. 8, Issue 4, Apr. 1980, pp. 369-379.

US Notice of Allowance on U.S. Appl. No. 13/574,158 DTD Jan. 28, 2013, pp. 1-10.

US Notice of Allowance on U.S. Appl. No. 13/574,158 mailed May 6, 2013, pp. 1-9.

International Preliminary Report on Patentability in PCT/CN2011/076488 dated Jan. 8, 2011.

Lee, H.M. et al., "Bipolar diffusion charging for aerosol nanoparticle measurement using a soft X-ray charger" Journal of Aerosol Science, vol. 36, Issue 7, pp. 813-829, Jul. 2005.

Pecora, R., "Dynamic Light Scattering Measurement of Nanometer Particles in Liquids," Journal of Nanoparticle Research, vol. 2, Issue 2, pp. 123-131, Jun. 2000.

US Notice of Allowance on U.S. App. No. 13/574,158 DTD Jan. 28, 2013.

US Notice of Allowance on U.S. Appl. No. 13/574,158 DTD Sep. 30, 2013.

US Notice of Allowance on U.S. Appl. No. 13/574,158 mailed Jun. 10, 2013.

* cited by examiner

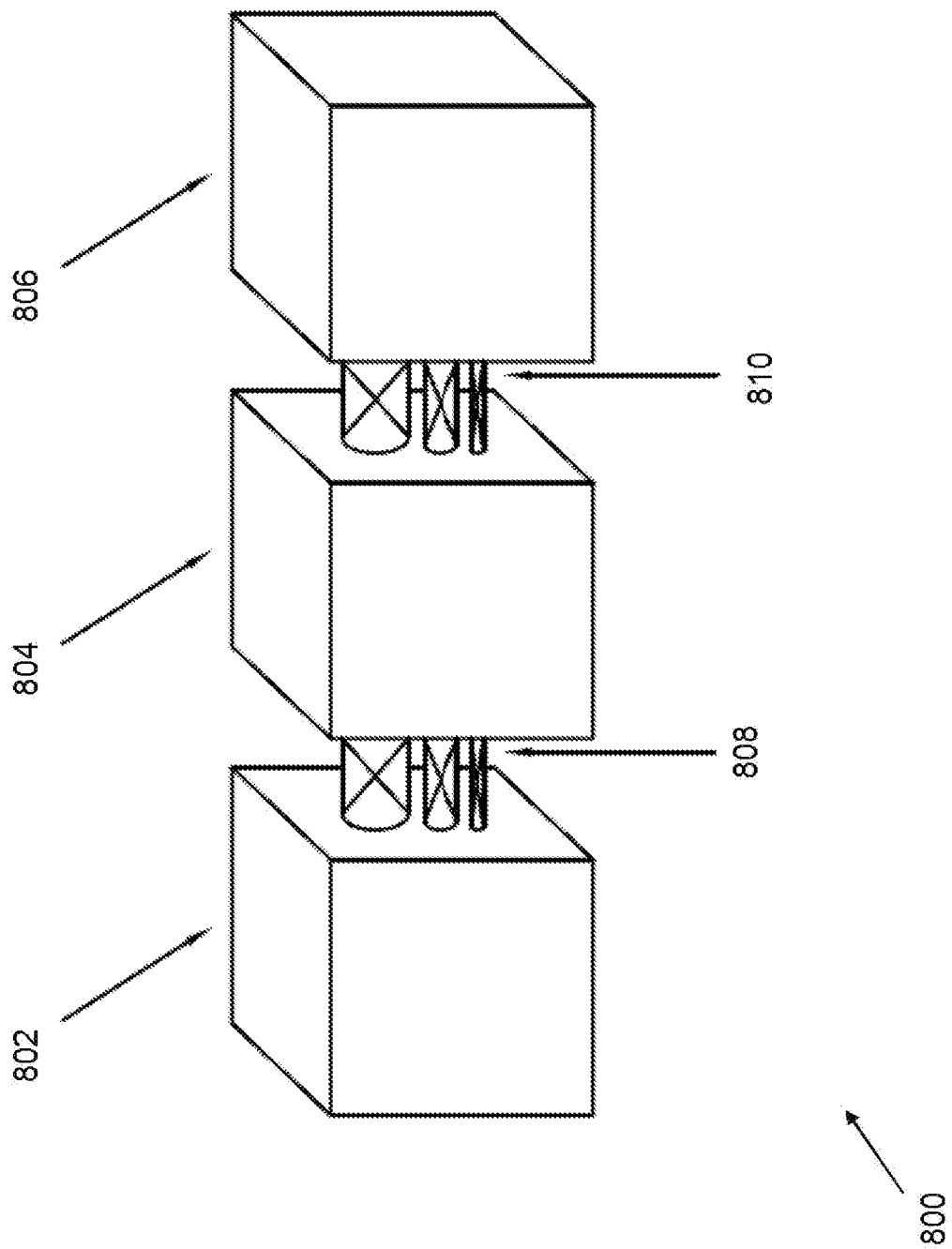

METHODS AND SYSTEMS FOR DETECTING OR COLLECTING PARTICLES

CROSS-REFERENCE TO RELATED APPLICATIONS

This application claims priority to PCT Application No: PCT/CN2011/076488 filed Jun. 28, 2011 entitled "Methods and Systems for Detecting or Collecting Particles and co-pending Chinese patent application serial number 201010214848.6 filed Jun. 29, 2010 entitled "Particle Measuring Apparatus and Method" by inventor Ma Yu-Chen, the contents of which are incorporated herein by reference.

TECHNICAL FIELD

The present disclosure is directed to methods and systems for detecting or collecting particles, particularly nanoparticles.

BACKGROUND

Unless otherwise indicated herein, the materials described in this section are not prior art to the claims in this application and are not admitted to be prior art by inclusion in this section.

Nanoparticles are finding increasing use in the marketplace, and can be made out of a wide variety of materials including carbon in the form of nanotubes and Bucky balls, metal oxides, semiconductors, and so on.

Questions have also been asked regarding the potential impacts of nanoparticles on human health, at least in part due to their very small size. For example, if nanoparticles enter the human body through the respiratory tract, it may be difficult for the human body to discharge them. Similarly, concerns have been raised about the potential absorption of nanoparticles through the skin, while larger conventional particles are not likely to fit through pores and channels in the skin. The fine particle size of nanoparticles also makes them challenging to filter or otherwise remove from the environment.

Conventional particle detection technologies are not effective at detecting or measuring the presence of nanoparticles.

SUMMARY

The applicant recognized that in various situations, e.g., during the production or testing process of nanomaterials, there is a need to monitor the emission of nanoparticles, or to collect the nanoparticles to thereby reduce their density in the environment. Accordingly, apparatus and methods are disclosed herein to effectively detect and/or collect nanoparticles, or other particles of small sizes in general.

In one aspect, an apparatus for detecting or collecting particles is described. The apparatus can comprise: a charger to electrically charge at least some of the particles; a collector to collect at least some of the charged particles; and a processor to obtain information indicative of an amount of the detected/collected particles based on measured electrical charges of the charged particles.

In an additional aspect, a method of detecting or collecting particles is described. The method can comprise: electrically charging at least some of the particles in a flow; collecting at least some of the charged particles; and obtaining information indicative of an amount of the detected/collected particles based on electrical charges of the collected charged particles.

An additional aspect describes a nanoparticle detector. The nanoparticle detector can comprise: a charger to electrically charge at least some nanoparticles passing through the detector; a collector to collect at least some of the charged nanoparticles; and a processor to obtain information indicative of an amount of the detected nanoparticles based on measured electrical charges of the collected charged nanoparticles.

Yet a further aspect describes a system for detecting or collecting particles. The system can comprise a plurality of apparatuses each comprising: a charger to electrically charge at least some of the particles; and a collector to collect at least some of the charged particles; and a processor to obtain information indicative of an amount of the detected/collected particles based on measured electrical charges of the charged particles from each of the plurality of apparatuses.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 8 shows an alternative diluter having multiple connectors with differing diameters.

DETAILED DESCRIPTION

Figure 1:
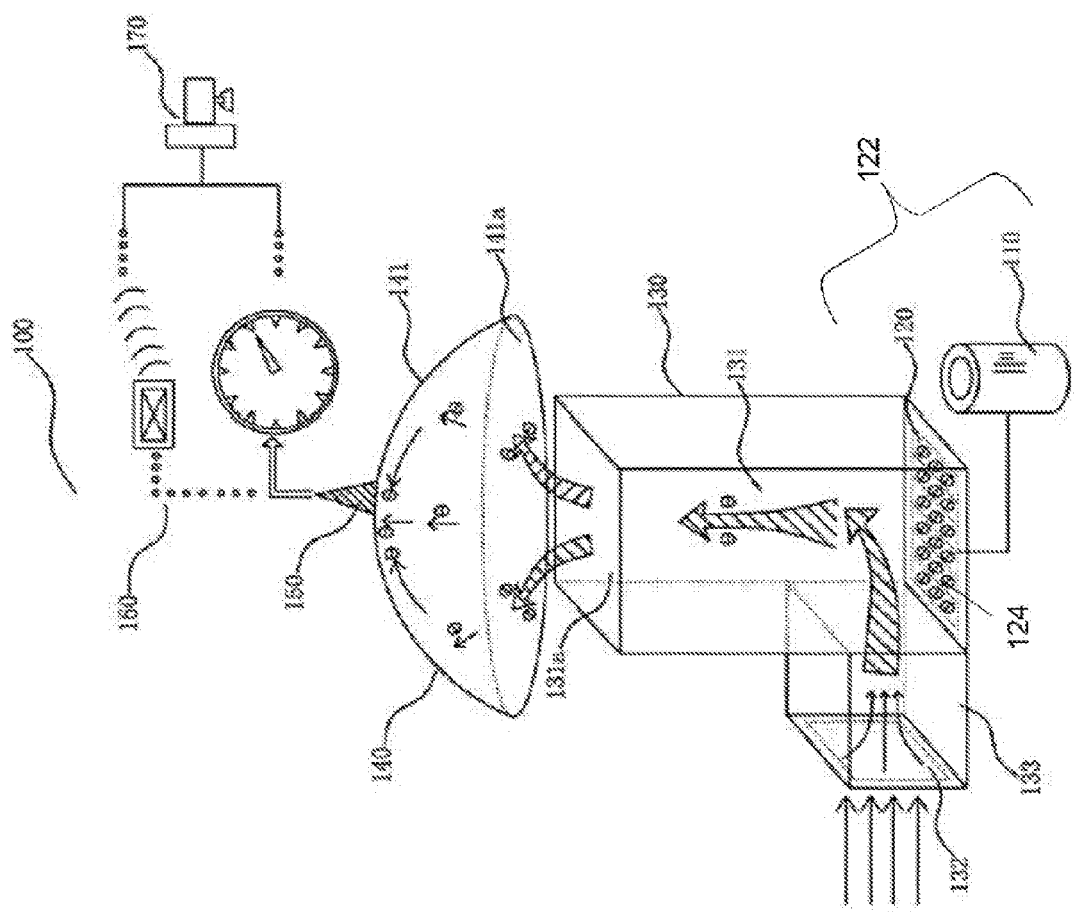
FIG. 1 shows an example system for the detection of nanoparticles in an airstream.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Methods, apparatus, systems, and devices related to detecting, measuring, and/or collecting particles are described. Generally, an apparatus can be used to perform detection and/or collection of particles. The apparatus can include at least one charger to electrically charge at least some of the particles, at least one collector to collect at least some of the particles, and at least one processor to obtain information indicative of an amount or concentration of the particles based at least in part on the measured electrical charges of the particles.

The systems and techniques described herein may be used to detect particles of generally any suitable size. In some embodiments, the particles may have a largest dimension of about 2500 nm or less, for example, in the range of about 100 nm to about 2500 nm. In some embodiments, the particles may have a largest dimension of about 1000 nm or less, for example, in the range of about 0.1 nm to about 1000 nm. Specific examples of the largest dimension include about 0.1 nm, about 1 nm, about 10 nm, about 50 nm, about 100 nm, about 200 nm, about 500 nm, about 1000 nm, about 1500 nm, about 2000 nm, about 2500 nm, and ranges between any two of these values. The particles may generally have any size distribution. The size distribution can be regular or irregular. The size distribution can be monomodal or multimodal.

Apparatus

FIG. 1 shows a possible high-level configuration design of an apparatus. For example, as illustrated in FIG. 1, an apparatus 100 can include at least one charger 122 to electrically charge at least some of the particles, at least one collector 140 to collect at least some of the charged particles, and at least one processor 170 to obtain information indicative of an amount or density of the detected/collected particles based on measured electrical charges of the charged particles. In some embodiments, a single processor may be connected to multiple detector units (e.g., a central located processor in a building may be connected to multiple detectors positioned throughout the building).

The apparatus 100 can generally be of any size, from small portable units to large, fixed installations. The apparatus 100 can be a miniature particle measuring device, where air flows carrying particles to be tested are allowed to pass through the particle channel 131 of the device body 130. The electrostatic generator 110 provides electrostatic charges, and the charge loader 120 loads particles to be measured with electrical charges.

The charger 122 can include at least one electrostatic generator 110, which can generate static electricity, and at least one charge loader 120 to load electrical charges to the at least some of the particles from the electrostatic generator 110.

For example, a van de Graff electrostatic generator can be used. The generator can operate at a variety of voltages. For example, the voltage can be about 10 V to about 10,000 V.

In one embodiment, the charge loader 120 can include an array of needles 124. The needles can generally have any size and dimension. In one example, the needles can each have a height of about 5 mm, and the array can have a size of about 2 cm×2 cm, containing 20×20 (400 total) needles. The needles can generally have any height. For example, the height can be about 0.05 mm to about 50 mm. In some embodiments, the needles can each have a height of 10 mm or less, 5 mm, or less, 1 mm or less, (e.g., in the range of about 1 mm to about 10 mm). In various embodiments the array may be square shaped, rectangle shaped, or any other suitable shape. In some embodiments, the length, width, or length and width, of the array may be less than about 10 cm, less than about 5 cm, less than about 2 cm, less than about 1 cm, or even smaller (e.g., in the range of about 1 cm to about 10 cm). With these relatively small exemplary dimensions, the charge loader 120 or the whole apparatus 100 can be made portable. Alternatively, a very large array size can be adopted for a fixed-position installation. In some embodiments, the array may include at least 100, at least 200, at least 400, at least 500, at least 1000 or more needles (e.g., in the range of 100-1000 needles). The needles can generally be made of any type of material suitable to facilitate loading charges to particles. For example, the needles can be made of copper, aluminum, silver, or other materials of high conductivity.

Figure 2:
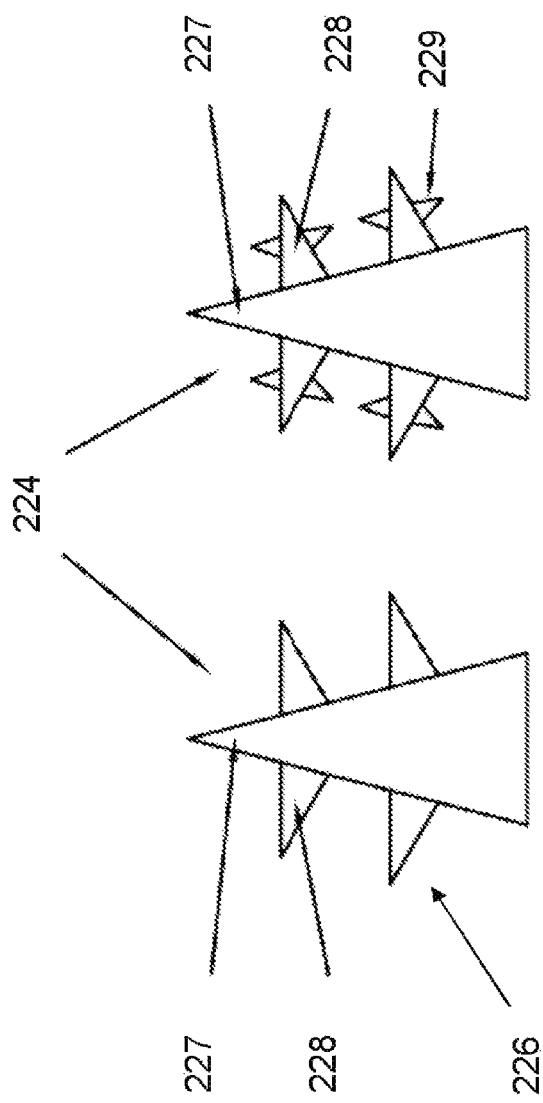
FIG. 2 shows a close-up view of needles having multiple branches that improve the charge loading efficiency.

The needles can be branched or unbranched. In one embodiment, with reference to FIG. 2, the needles 224 each include a plurality of branches 226 resembling tree branches, to improve charge loading efficiencies. In the examples shown, the needles 224 can include a first level point discharge structure 227, a second level point discharge structure 228, and a third level point discharge structure 229. In various embodiments, additional levels of point discharge structures may be used. In one example, the needles 224 can have a total length of about 1 mm to about 100 mm, and the branches 226 can have a branch length that is about 20-80% of the total length of the needles 224. The third level point discharge structure 229 can have a dimension that is about 20-80% that of the branch length of the branches 226.

Figure 3:
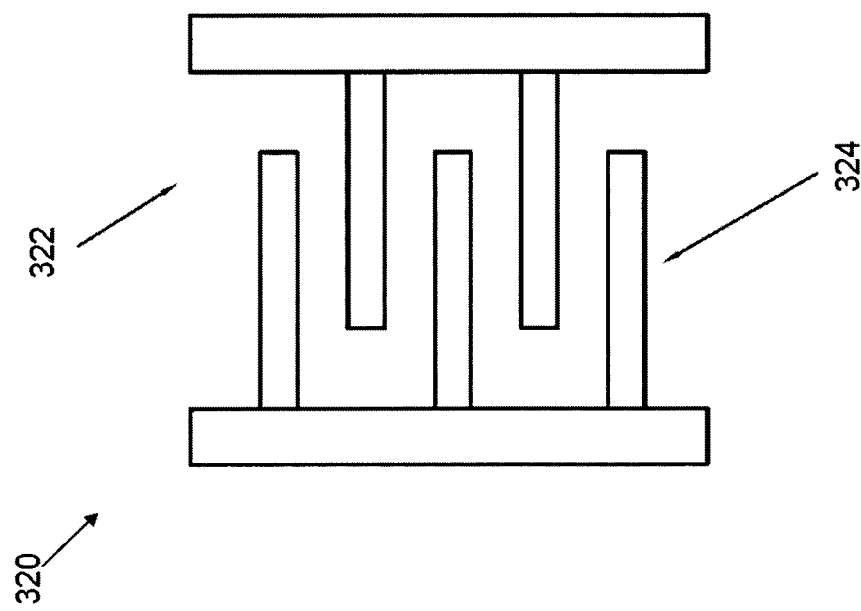
FIG. 3 shows a possible charge loading structure design including interlacing fingers or plates.

The charge loader 320 can have a variety of structures. In one embodiment, with reference to FIG. 3, a charge loader 320 can have an interlacing charge loading structure 322 including a plurality of interlacing fingers or plates 324. These fingers or plates increase the surface areas of the charger, and improves the probability of the particles coming into contact with the surfaces, thereby improving the charge loading efficiencies. The gaps between the fingers or plates 324 can be about 5 to about 300 mm, for example, and the length of the fingers or plates 324 can be about 1 to about 4 times the dimension of the gaps.

Figure 4:
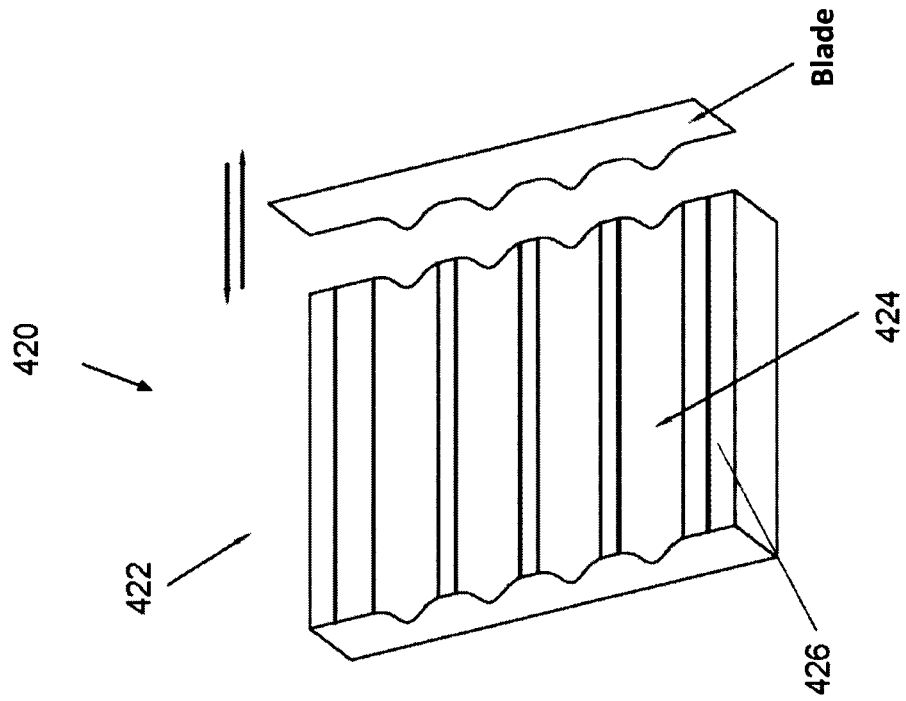
FIG. 4 shows a possible charge loading structure design including a grooved surface.

Alternatively, in some embodiments, a charge loader 420 can have a grooved charge loading structure 422 including a plurality of grooves 424 on a metal surface 426. FIG. 4 shows an example of such a grooved structure. In some embodiments, the grooves 424 can be molded into the loading structure. In some embodiments, the grooves 424 can be, for example, freshly scratched on the metal surface 426 using a blade 428, for example before each use, to improve the charge loading efficiency. The blade 428 can be driven by a motor or an actuator.

The channel 131 can include at least one particle discharge port 131a and at least one particle feed port 132. The various ports can generally be of any size and shape. Shapes are typically regular geometric shapes such as square, round, or rectangular shapes, although other regular or irregular shapes may be used. In one example, the particle feed port 132, which allows air or other gaseous medium containing the particles to enter, has a square opening of 2×2 cm, although any other suitable shape and dimensions may be used. The smaller opening is suitable for a portable device, and larger opening can be used for fixed installation. The channel can be made of ceramic, metal, plastic, or any other suitable materials.

At least one filter layer 133 can be optionally included to select particles based on particle size. For example, large particles that do not need to be measured can be kept out of the channel 131. In one embodiment, the filter is configured to prevent particles larger than a threshold size (e.g., 1 nm, 10 nm, 100 nm, 1000 nm, e.g., in the range of 1-1000 nm) from being electrically charged by the charger 122. The filter 133 can further reduce a density of the particles in the flow. In some embodiment, the filter 133 also acts as a diluter to reduce the particle density, although it may change the particle size distribution. The filter can have a square shape, for example, with a size of about 5-200 mm, or a circular shape with a diameter 5-200 mm in another example. The filter can be an off-the-shelf product, such as a HEPA or ULPA filter. The filter class can be selected to be suitable for filtering or selecting the desired particle types and sizes. The filter and the channel can be selected to have matching shapes and sizes.

If the filter layer 133 is not used, unwanted data related to particles larger than the target size can be eliminated through data analysis. For example, particles of larger sizes have a higher probability of receiving loaded static electricity because of their larger surface areas. As there is repulsion between static electricity, when the repulsion reaches equilibrium, a positive correlation can form between the loading quantity of static electricity and the surface area of particles. Data of the particles of a specific size range can then be derived based on the correlation. In one example, a method is provided including (i) determining a threshold range for the electrical pulses to be collected, such as electrical charges in the range of $1.6 \times 10^{-18}$ C-$1.6 \times 10^{-13}$ C; (ii) measuring electrical pulse data; and (iii) determining whether the electrical pulse is within the threshold range determined in (i). If yes, then the data is collected. If not, then the corresponding electrical pulse data is deleted.

The channel 131 allows the particles to flow therethrough, for example carried by airflow or a flow of a gas such as nitrogen. The charged particles can also be driven by the charge loader 120, as these particles have the same polarity as the charge loader 120, and thus are driven by the charge loader 120 through Coulomb repulsion.

Figure 5:
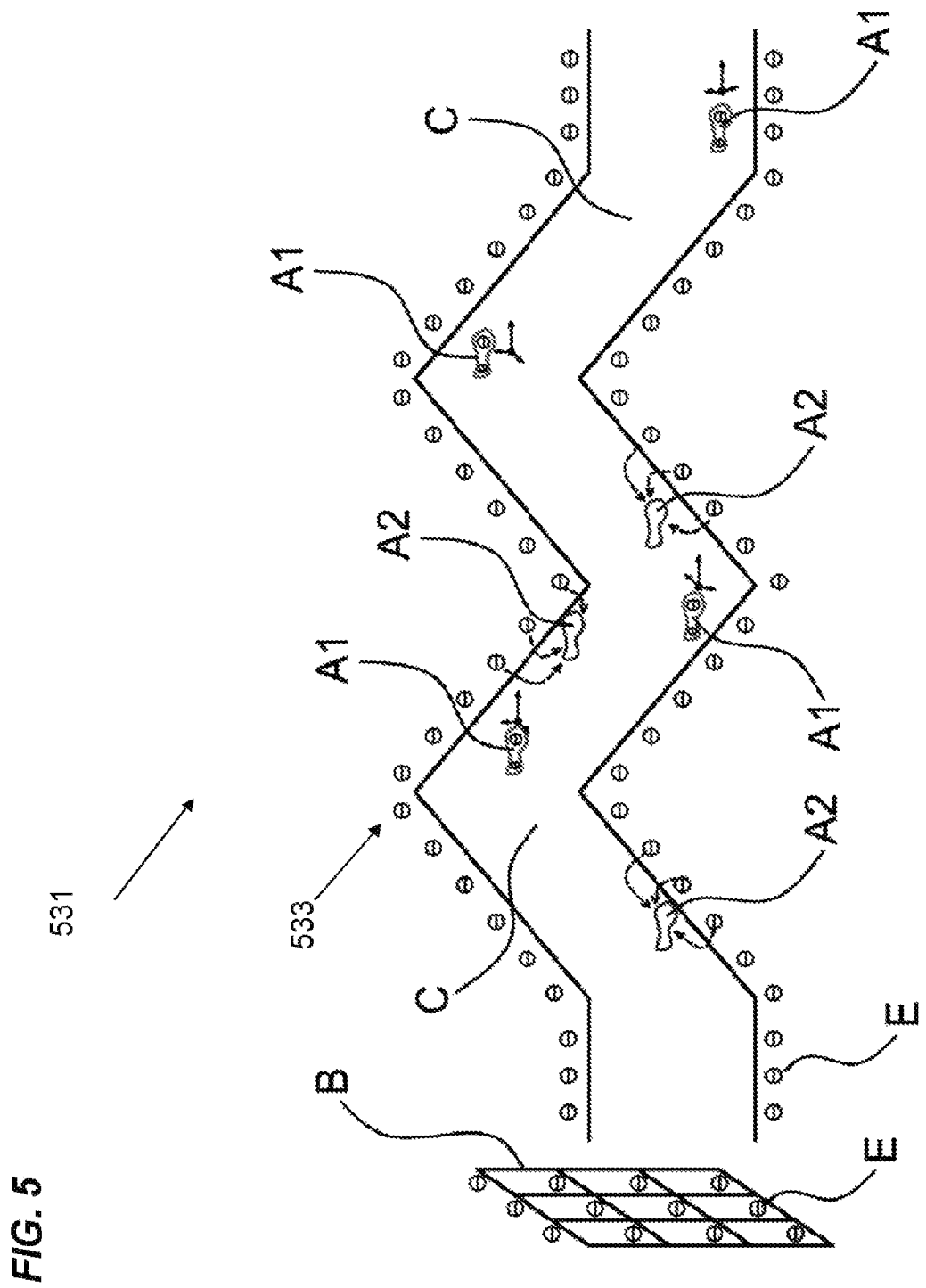
FIG. 5 shows an electrically-charged bent or torturous channel portion that can charge particles.

The channel can be straight or not straight in shape. For example, as illustrated in FIG. 5, the channel 531 can include at least one electrically-charged bent or torturous portion 533, which is configured to charge at least some of the particles to the same polarity as the charger.

As the particles pass through the charge loader, e.g., the like-charge source (B), the negative charges (E) can be transferred to some of the particles. In some other embodiments, positive charged may be used. The bent or torturous portions in the channel 531 form one or more meander cavities (C), and increase the ratio of the particles loaded with electric charges (A1) to the particles not loaded with electric charges (A2).

Specifically, after the like-charge source (B) preliminarily loads particles with electric charges (E), particles loaded with electric charges (A1) will unlikely fall on the wall of the meander cavity (C) due to the Coulomb repulsion, and move along the channel 531 towards the outlet under the influence of the electric field of like-charge source (B) or following the flow of air (or other gas). On the other hand, the particles not loaded with electric charges (A2) tend to be trapped within the meander cavity (C) and may come into contact with the wall of meander cavity (C) to be electrically loaded by the charged wall of meander cavity (C).

Advantageously, the structure facilitates rapid release of particles loaded with electric charges, with the help of Coulomb repulsion, and at the same time rapidly loads those uncharged particles with electric charges.

In various embodiments, the tortuous portion 533 includes at least 1, at least 2 at least 3, at least 4, at least 5 (as shown), at least 10, or more than 10 bends. In various embodiments, the bends may each be at an angle greater than 5, 10, 15, 20, 25, 30, 35, 40, 45, 50, 55, 60, 65, 70, 75, 80, 85, 90, or more degrees.

Figure 6:
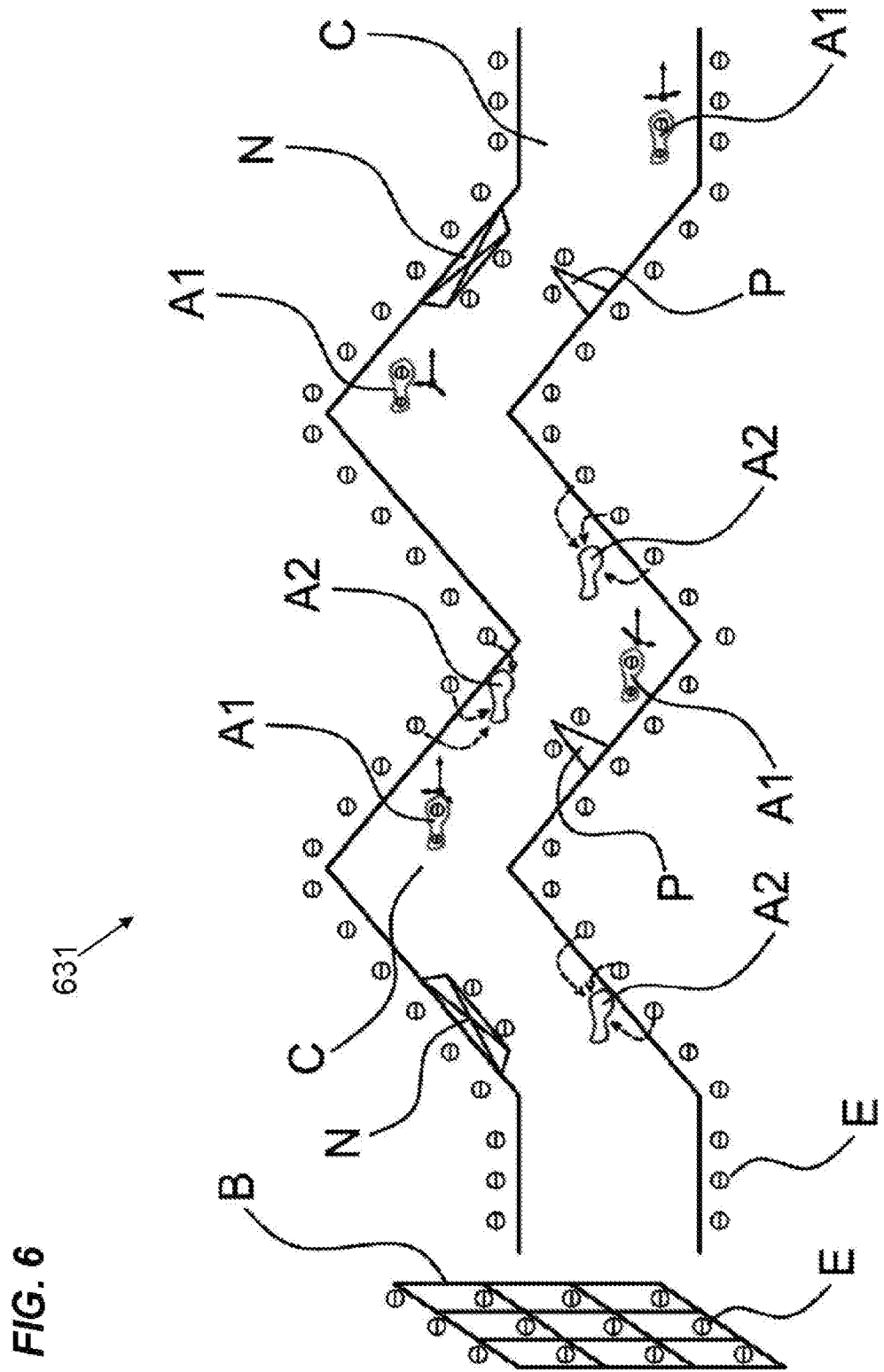
FIG. 6 shows a channel portion having one or more electrically-charged protrusions that can charge uncharged particles.

The channel can optionally include one or more protrusions. For example, as shown in FIG. 6, the channel 631 includes at least one electrically-charged protrusion (N, P) configured to further charge at least some of the uncharged particles in the flow. The protrusion can include, for example, a plurality of needles (P) capable of transferring electrical charges to the uncharged particles (A2) through point discharges, or a plurality of protrusions forming a conductive network (N) to conduct electrical charges to the uncharged particles (A2).

In some embodiments, the needles (P) can have cone shapes with a bottom diameter of about 1 mm to about 5 mm and a height of about 1.5 to about 3 times the bottom diameter. In some other embodiments, the conductive network (N) can be made of copper wires having a diameter or width of about 0.02-0.2 mm. In one example, copper wires with a diameter of 0.05 mm form a mesh having openings with a size of 0.25× 0.25 mm. The mesh can have a total area of 5 mm×5 mm, for example.

Figure 7:
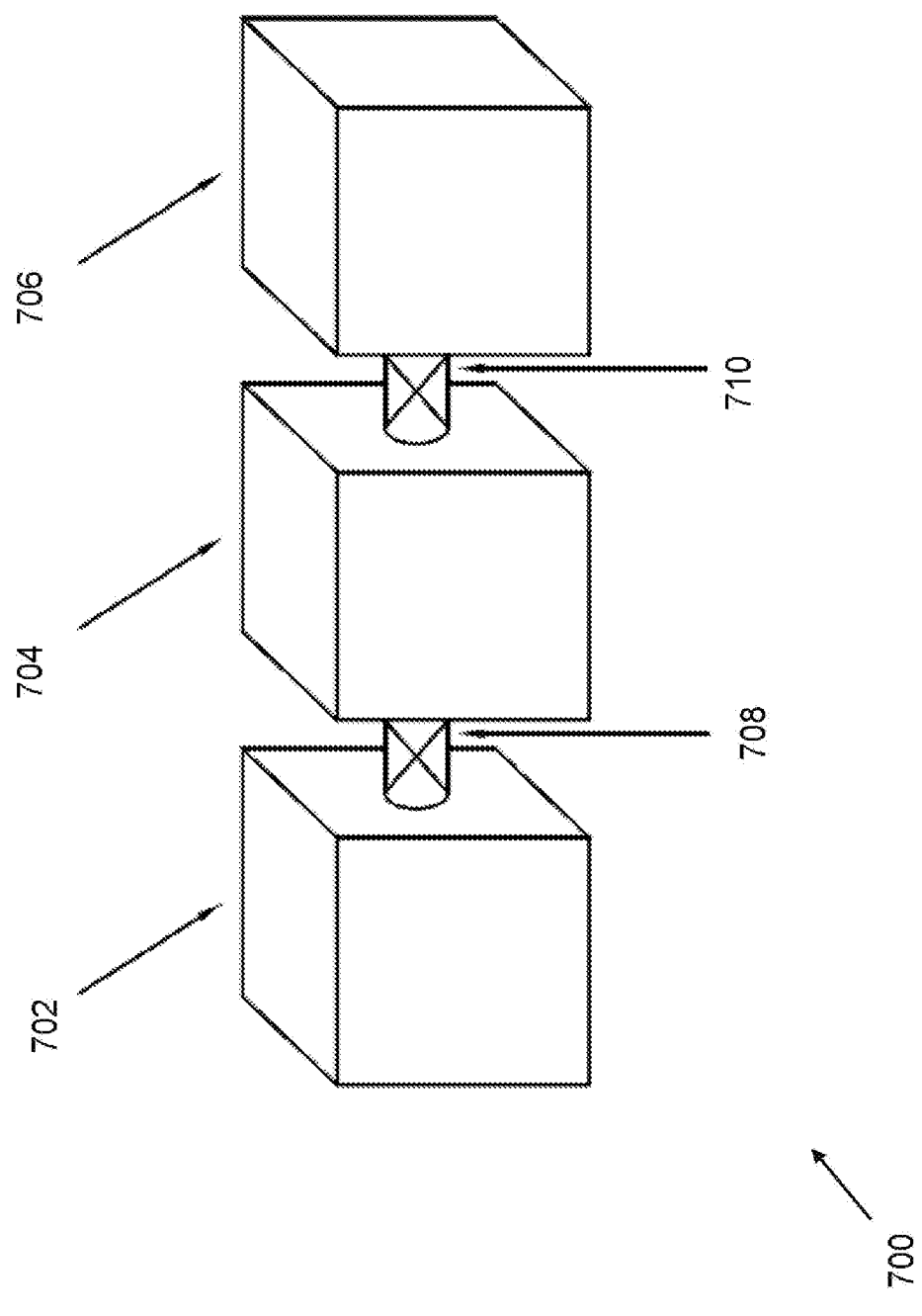
FIG. 7 shows a diluter that can optionally be used to reduce the density of particles being measured and to improve accuracy of resulting measurement when the input particle density is high.

The apparatus can optionally include at least one diluter. A diluter can be desirably used when samples have high concentrations of particles. For example, as shown in FIG. 7, a diluter 700 can be included in the channel 131 or connected to the channel 131 to reduce the density of the particles being measured, to thereby improve the measurement accuracy, e.g., by reducing the density of the electrical pulses when they become too crowded. A diluter can also function to reduce the likelihood of particle aggregation. The diluter can have various configurations. In the embodiment shown in FIG. 7, the diluter 700 includes a first grading chamber 702, a second grading chamber 704, and a third grading chamber 706. These diluting chambers can be connected by control valves 708, 710, which selectively allow pneumatic communication between the chambers. In various embodiments, any other suitable number of chambers and connections may be used.

In one example, the first grading chamber 702, the second grading chamber 704, and the third grading chamber 706 each have a volume of about 5 cm³. The control valves 708, 710 each have a volume of about 0.05 cm³. Valves can be disposed on both sides of the control valves 708, 710, between neighboring chambers. The operation can be realized in the following example steps: (A) opening the first grading chamber 702 and the control valve 708, letting in the flow of air or gas to be detected; (B) closing valve between the first grading chamber 702 and the control valve 708; (C) opening the valve between the second grading chamber 704 and the control valve 708. In one example, the 0.05 cm³ gas expands in the second grading chamber 704, reaching a total volume of 5.05 cm³, i.e., 101 times its original volume. Thus, through this dilution process, the particle density is diluted by a factor of 101. Similarly, through the control valve 708 and the third grading chamber 706, the gas is further diluted by a factor of 101.

The second grading chamber 704 and the third grading chamber 706 can be pre-evacuated to a near vacuum state. Otherwise, if there is residual gas in these chambers, these chambers may be at least cleaned to reduce residual particles in these chambers, to reduce interference with the measurements. To clean the chambers, a clean air flow can be directed to "wash" the chambers. Other cleaning methods can also be used.

In one embodiment illustrated in FIG. 8, the diluter 800 includes groups of connectors 808, 810 disposed between the grading chambers 802, 804, 806. Each of the groups 808, 810 includes a plurality of connectors having different diameters. In various embodiments, any other suitable number of chambers and connections may be used.

The operation principle of the diluter 800 is similar to that of the diluter 700. With the disposition of different connectors having different volumes, the dilution factor can be further adjusted. This is because the dilution factor between adjacent stages can be determines as the sum of the volume of the chamber and the volume of the connector divided by the volume of the connector. Thus, by selecting the different connectors, different dilution factors can be selected.

Figure 9:
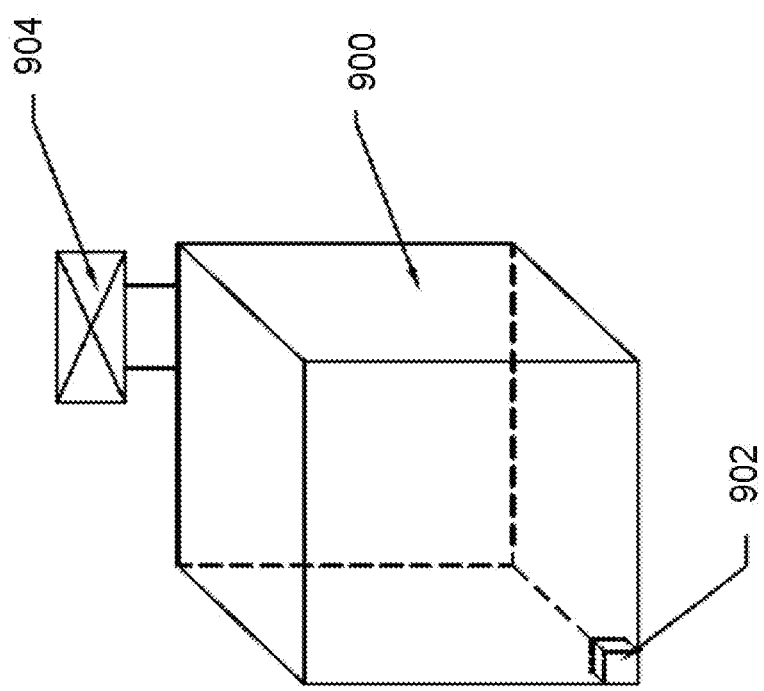
FIG. 9 shows a possible chamber and sub-chamber design that can be used to reduce particle density.

In one embodiment shown in FIG. 9, a diluter includes at least one chamber 900 and at least one sub-chamber 902. The various chambers can generally be any size and shape. The shape of the chambers typically will be regular geometric shapes such as cubes, spheres, or cylinders, although other regular or irregular shapes may be used. The chamber 900 can be first filled with the air or gas to be detected, with the sub-chamber 902 communicative with the chamber 900. The sub-chamber 902 can then be isolated from the chamber 900, and the chamber 900 evacuated by a vacuum valve 904. Subsequently the sub-chamber 902 can have its content released into the chamber 900, resulting in a diluted content, e.g., reduced particle density.

Alternatively, the sub-chamber 902 can be filled with the air or gas to be detected, and the chamber 900 can be evacuated or filled with a particle-free gas. Subsequently, the sub-chamber 902 can have its contents released into the chamber 900, resulting in a diluted content. In either configuration, the known volumes of the chamber 900 or sub-chamber 902 can be used to calculate the dilution factor of the particle concentration. For example, if the volume of the chamber 900 plus sub-chamber 902 is ten times the volume of the sub-chamber 902, then the dilution factor is 10×.

The dilution process can include further stages. For example, after the above steps in a first stage of dilution, the valve between the sub-chamber 902 and the chamber 900 can be closed again, and the chamber 900 can be further evacuated to a near-vacuum state. Next, the valve between the sub-chamber 902 and the chamber 900 can be opened again to connect the sub-chamber 902 and the chamber 900. Thus, the particle density is further diluted by another factor of 10 in the second stage of operation.

For each stage of dilution, the dilution factor is (the volume of the sub-chamber 902+the volume of the chamber 900)/(the volume of the sub-chamber 902). In one example, the volume of the chamber 900 is 1000 cm$^3$, and the volume of the sub-chamber 902 is 1 cm$^3$. After the first stage of dilution, the particle density is reduced by a factor of 1001. After the second stage of dilution, the density is diluted by another factor of 1001. That is, the particle density is reduced to about one millionth of its original value.

The volume of the various chambers can generally be any volume. The volumes can be selected at least in part on the desired portability of the apparatus, and of the expected particle density of samples to be measured. In various embodiments any other suitable dimensions or shapes may be used.

Figure 10:
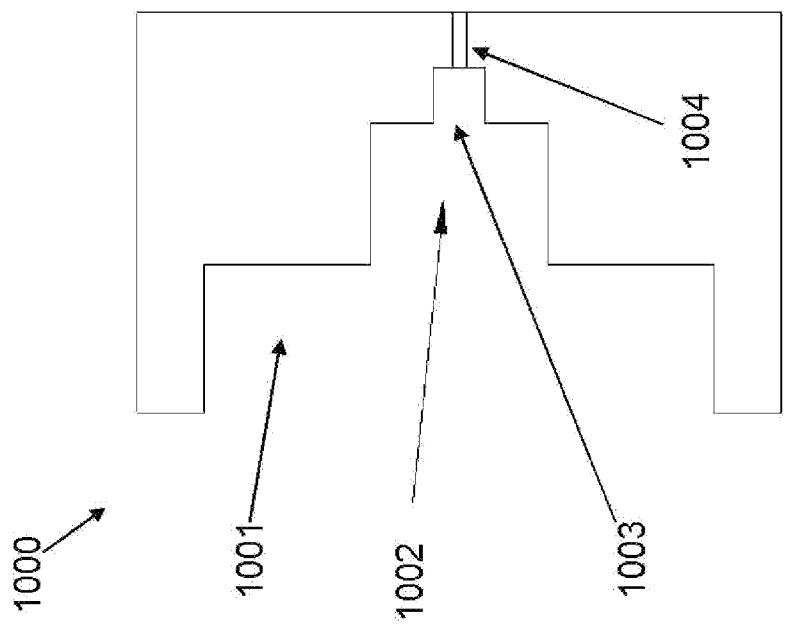
FIG. 10 shows an alternative diluter design that includes multiple grading channels of different diameters.

In an example illustrated in FIG. 10, a diluter 1000 can optionally include a plurality of grading chambers 1001, 1002, 1003, each having a different diameter/volume, and a sub-chamber 1004 connected to the smallest chamber 1003.

An inner valve (not shown) is disposed between the sub-chamber 1004 and the smallest chamber 1003. An outer valve (not shown) is disposed outside the sub-chamber 1004. During operation, the inner valve is first closed. The grading chambers 1001, 1002, and 1003 are evacuated, and one of the grading chambers is selected as an exiting chamber. The gas to be diluted is introduced to the sub-chamber 1004, and the outer valve is closed. The inner valve is then opened, and the gas to be diluted is introduced into the selected exiting chamber. Thus, the gas is diluted, and the dilution factor can be calculated using the formula similar to those described above with respect to FIGS. 7, 8, 9. The non-graded particles can be washed out using a flow, such as a clean air or a clean fluid. Alternatively, the various chambers can be evacuated to a near-vacuum state. During the evacuation process, the non-graded particles can be removed.

In one example, the first grading channel can have a cross section of 10 cm$^2$, the second grading channel can have a cross section of 0.5 cm$^2$, and the third grading channel can have a cross section of 0.5 cm$^2$. Thus, after passing through the grading channels 1002, the particle density is diluted by a factor of 1,000. The geometry and the size of the grading channels 1002 can be designed based on the required measurement accuracy, and the size of the device 100. In various embodiments, any other suitable dimensions or shapes may be used.

When particles carrying the electrostatic charges reach a charged particle receiver 140 after passing through the particle discharge ports 131a, the receiver 140 can collect the charges, for example, through skin effects (e.g., the tendency of an electric current or magnetic flux to distribute itself within a conductor with the current density being largest near the surface of the conductor, decreasing at greater depths.) The quantity of charges collected by the receiver 140 can then be measured directly by the receiver 140. Alternatively, a discharge assembly performs electric discharge and measurement. Data indicative of the quantity of the collected charged particles can be obtained through measurement of charge pulses, and converted to data indicative of the properties of the particles. A pulse threshold can be set such that only electrical pulses above a pulse threshold are recorded as valid data, to avoid recording electrical pulse noises.

Ideally, individual electrical charges are measured through the measurement of the pulses. If the particle density is very high, a single pulse can be a result of multiple charged particles, and the accuracy of the detection of the nanoparticles can be increased through the dilution of the particle density as described above.

The pulse strengths result from the net electrical charges deposited on the particles. These net electrical charges mostly are distributed on the surfaces of the particles. The pulse strengths indicate the measurable number of net electrical unit charges, or the measurable electrical charges. In one example, a single pulse corresponds to 10-1,000,000 electrical unit charges, or an electrical charge of about $1.6 \times 10^{18}$ C- $1.6 \times 10^{-13}$ C.

As an example, the receiver 140 can be a conductive, spherical or elliptical shell with an open end, which corresponds to the particle discharge port 131a. The receiver 140 typically can be larger in cross-section than the particle discharge port. In one example, the receiver and the particle discharge port can have the same cross-section shape, such as circular.

A charge exporter assembly 150, which in one embodiment is a discharger having a pointed-end structure, can be used to export electrical charges from the receiver 140. The exported charged can be measured by a charge measuring assembly 160, which can measure charges based on at least one of Coulomb repulsion, charge movement in a magnetic field, charge movement in an electric field, or effect of charges on capacitance changes.

In one embodiment, the charge measuring assembly 160 can be maintained at a specified distance to the pointed end of the discharger, and the repulsive or attractive force due to the electrical field is used for measurements. The repulsive force results from electrical charges of the same polarity, and the attractive force results from electrical charges of opposite polarities. For the discharger in the charge exporter assembly 150, as a result of the point discharge effect, the electrical field adjacent the pointed end is the strongest. For example, at a close range, such as within 0.1 mm, the electrical field potential can be in the range of about 0.1-1000 V. In one embodiment, a negatively-charged probing needle can be disposed adjacent the pointed end of the discharger, and senses the force. Based a predetermined correlation between the force and the electrical charges, the electrical charges from the pulses can be measured.

Skin effects can be used to trap electric charges, for example, using a conductive, semi-enclosed spherical shell 141 having the charged particles move along a surface thereof. If electric charges are conducted within the spherical shell 141, the electric charges tend be dispersed throughout the surface of the conductive shell 141 due to Coulomb repulsion.

A grounding device can optionally be provided to couple the receiver 140 to the ground. When the receiver collects a large amount of electrical charges, measurement accuracy can sometimes be negatively affected. By releasing the electrical charges on the surface of the receiver 140 to the ground, the measured charge may be "zeroed," thereby improving the measurement accuracy.

Figure 11:
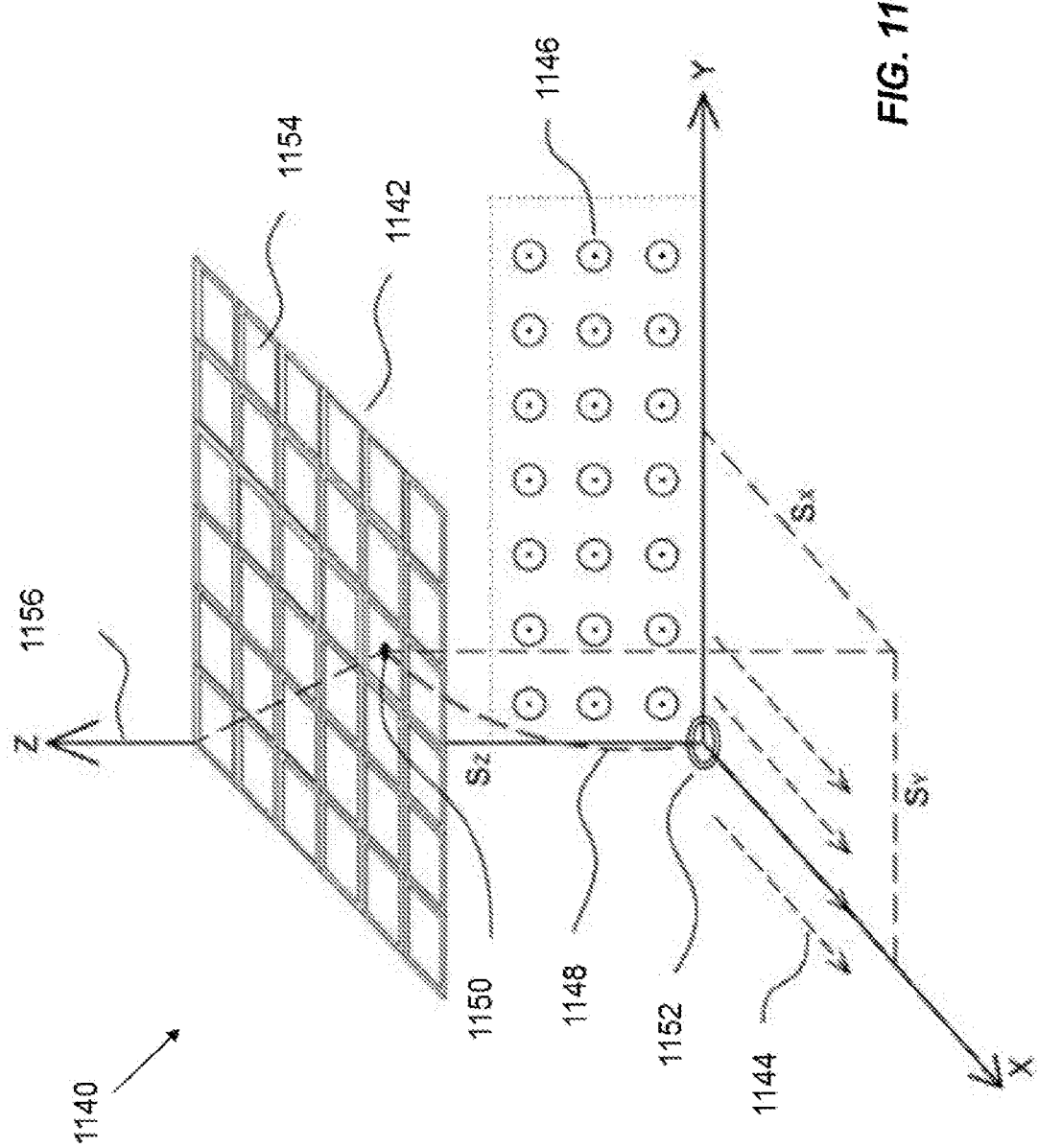
FIG. 11 shows a possible receiver design including a conductive mesh that can collect charged particles.

The receiver 1140 can optionally include a conductive mesh 1142 to collect the charged particles, as shown in FIG. 11. The receiver 1140 can further include at least one electric field generator to generate an electric field 1144, and/or at least one magnetic field generator to generate a magnetic field 1146 (or combinations thereof), to modify trajectories 1148 of the charged particles 1150. The charged particles 1150 enter the collector 1140 from the entrance 1152, pass at least a portion of the charge receiver units 1154, and are emitted in the general direction 1156. The entrance 1152 can be configured to allow particles of specific mass and/or electric charges to pass therethrough, for example by selecting a combination of the entrance size and the strength of the magnetic field/electric field strength at the entrance. The receiver units 1154 of the conductive mesh 1142 can be scanned to obtain the electrical pulses generated by each unit.

In one example, the charge receiver units 1154 are independent and insulated from each other. Each of the charge receiver units 1154 can be coupled to a corresponding electrical charge measurement unit. The electrical charge measurement unit can measure electrical charges based on the repulsive or attractive forces between charges, or by measuring an electrical capacitance after collecting the electrical charges. Other measurement methods can also be used.

Each of the charge receiver units 1154 has a predetermined position. Thus, by measuring the different electrical charges through the different charge receiver units, the positional changes (as influenced by the electrical field and the magnetic field) and charges of the charged particles 1150 can be effectively measured.

While not wishing to be bound by theory, the number and/or masses of the charged particles can be optionally calculated from the measured electrical pulses based on the following formulae.

The Coulomb force in the X direction is:

$$F = E_o q_p. \quad (1)$$

In the X direction, $$F_X = m_p a_X, \quad (2)$$

where $a_x$ is the acceleration of the charged particle in the X axis. Thus, $$a_X = \frac{E_o q_p}{m_p}. \quad (3)$$

Assuming a zero velocity of the charged particle in the X direction, the distance traveled by the charged particle in the X direction is $$S_X = \frac{1}{2} a_X t^2 = \frac{1}{2} \frac{E_o q_p}{m_p} t^2, \quad (4)$$

from which it can be obtained that $$t = \sqrt{\frac{2 S_X m_p}{E_o q_p}}. \quad (5)$$

In the Z direction, the velocity is the same as the initial particle velocity:

$$v_z = v_o. \quad (6)$$

Neglecting the effect of gravity, $$v_o = v_z = \frac{S_z}{t} = \frac{S_z}{\sqrt{\frac{2 S_X m_p}{E_o q_p}}}. \quad (7)$$

In the YZ projection plane, $R_p$ is the radius of the circular motion of the charged particle under Lorentz force, and $$R_p = \frac{m_p v_o}{B_o q_p} = \frac{m_p}{B_o q_p} \cdot \frac{S_z}{\sqrt{\frac{2 S_X m_p}{E_o q_p}}} = \frac{S_z \sqrt{m_p}}{B_o \sqrt{\frac{2 S_X q_p}{E_o}}}. \quad (8)$$

It can be further obtained that $$\sqrt{\frac{m_p}{q_p}} = \frac{\sqrt{S_X^2 + S_Y^2} \times B_o \sqrt{\frac{2 S_X}{E_o}}}{S_z}, \quad (9)$$

where $$R_p = \sqrt{S_X^2 + S_Y^2}. \quad (10)$$

Thus, $$m_p = (S_X^2 + S_Y^2)\frac{2B_o^2 S_X}{E_o S_Z^2}q_p. \quad (11)$$

Accordingly, using the charges $q_p$ measured through the collector 1140 shown in FIG. 11, the charged particle mass $m_p$ can be obtained.

When the effect of gravity is taken into consideration, the above formulae can be modified by including the acceleration of the particle in the Z direction as affected by the gravity.

The particle analysis assembly 170 can optionally include at least one processor to analyze the data measured by the charge measurement assembly 160. In one embodiment, the particle analysis assembly 170 includes a direct particle analysis module for indicating particle status corresponding to the reception status of quantity of charges, and an indirect particle response module for deriving the overall status of particles through the proportion of charged particles. The processor can be co-located locally with the collector 140, or can be remotely located.

Based on the known correspondence between charge pulses and particles to be measured, the types of particles can also be determined. For example, the types of the particles can be derived from the electrical charges they carry and their masses. Under the same conditions, the electrical charges can be proportional to the particle surface area. Based on the particle surface area, the particle volume can be derived. From the particle volume and mass, the particle density can be obtained. Thus, in addition to the number of particles, the embodiments disclosed herein can also provide information on the particle size and mass.

Advantageously, the various configurations disclosed herein can load particles with electric charges efficiently by using either or both the charger 122 and the bent or torturous portions 533 of the channel 131. In addition, the charger 122 also drives the charged particles along the channel 131 through Coulomb repulsion, as the charged particles and the charger have the same polarity. The meander cavity formed by the bent or torturous portions 533 of the channel 131 has its wall charged to the same polarity as the charger and the already-charged particles. Thus, charged particles tend not to come into contact with the side wall of the channel 131 as a result of the Coulomb repulsion, whereas uncharged particles would be effectively charged by the side walls of the channel. Uncharged particles tend to be trapped in the meander cavities before they are being charged.

Methods

Various methods of detecting and/or measuring particles are described. Particles may be provided in a sample to be tested. The sample can generally be any sample containing or suspected of containing particles. Examples of samples include air samples, automotive exhaust, industrial exhaust, semiconductor manufacturing exhaust, roadside exhaust, etc. In addition, the sample can be from an industrial manufacturing product, from which the particle characteristics can be measured to determine whether the particles in the product are within the specification of the requirements on the granulation.

Figure 12:
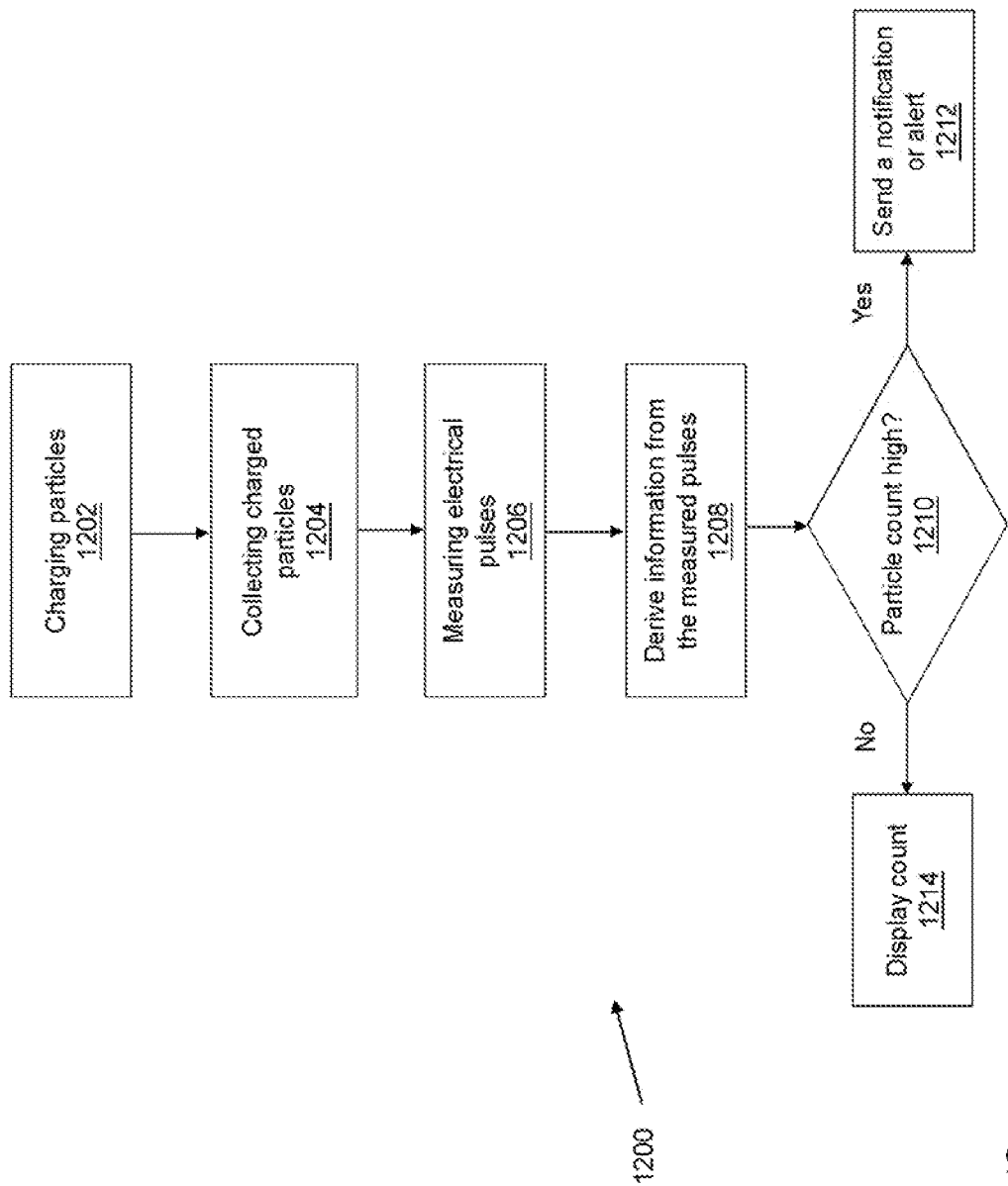
FIG. 12 shows a flowchart of steps that can be used to detect and measure nanoparticle concentrations in a sample. The method can result in a nanoparticle count being displayed or communicated. The method can additionally or alternatively result in a notification or alert being issued if the nanoparticle count meets or exceeds a predetermined value, or if the rate of change in nanoparticle counts over time meets or exceeds a predetermined value.

An example method 1200 of detecting particles is illustrated by the flowchart in FIG. 12, although various additional or substitute steps may be used. In an operation 1202, at least some or all of the particles in a flow are electrically charged. In an operation 1204, at least some or all of the charged particles are collected. In an operation 1206, electrical pulses resulting from the charged particles are recorded and measured. In an operation 1208, information indicative of an amount of the detected/collected particles are derived based on the measured electrical charges of the collected charged particles. In an operation 1210, the obtained information such as the particle count and/or rate of change in particle count is compared with a threshold. The particle count can be stored and/or displayed to a user in operation 1214. If the particle count or rate exceeds the threshold, in step 1212, a notification or alert is sent. The notification or alert can be in place of or in addition to the storing or displaying step.

In various embodiments, any other suitable display, control signal, alarm signal, etc. may be generated based on the detected particle count information. The particle count may be processed to provide any suitable information (e.g., particle density). For example, the particle density may be derived based the particle count and the relevant sample volume.

In one example, if one measurement takes about 10 microsecond, then during each second 100,000 measurement operations can be performed, such that the maximum detected particle number is on the order of 100,000. The detected electrical charges can be in the range of about $1.6\times10^{-18}$ C-$1.6\times10^{-13}$ C, for example. The low end of this range corresponds to detection of only a few elemental charges (the elemental charge being about $1.6\times10^{-19}$ C. The upper end of the range corresponds to detection of about 100,000 charges, i.e., detecting charge for every or nearly every measurement during the one second period. In other embodiments, other measurement speeds may be used.

The detection of the current pulses caused by the collected charged particles can be based on a Coulomb repulsion between charged particles, a movement of charged particles in a magnetic field, a movement of charged particles in an electric field, or a change in capacitance due to the charged particles.

The method can further include determining a detection threshold of the current pulses. A correlation between particle count or density information and electrical charges may be predetermined, for example based on the formulae described above. When the same type particles are in a same state, e.g., the particles being detected or measured are a same type of particles or having similar properties and sizes, the measured electrical charges are proportional to the particle count or density. If an air or gas content includes particles of different sizes or types, the correlation may be more complex than a linear proportionality.

In one example, a user needs to detect silicon dioxide particles having roughly a uniform size of about 50 nm. If the measured electrical charges are $2\times10^{-13}$ C per second, then the corresponding particle density is about $5\times10^7/m^3$. If the measured electrical charges reach $6\times10^{-13}$ C per second, then the corresponding particle density is about $1.5\times10^8/m^3$, i.e., three times its earlier value.

The method can optionally include measuring electrical charges at a plurality of locations, such as by setting up a plurality of sampling orifices at different locations within a factory or a laboratory, and processing measured data from the plurality of locations using a single processor. In another example, a system is provided for detecting or collecting particles. The system includes a plurality of apparatuses each including at least one charger to electrically charge at least some of the particles, and at least one collector to collect at least some of the charged particles. A processor of the system can centrally obtain information indicative of an amount of the detected/collected particles based on measured electrical charges of the charged particles from each of the plurality of apparatuses. This can reduce the cost as the processor and the analysis software may in some cases be a significant portion of the cost of the system.

In some other embodiments, a sample is obtained from a flow of particles and divided into a plurality of volumes. A set of data indicative of an amount of the detected/collected particles based on electrical charges of the collected charged particles from each of the plurality of volumes are measured, and a statistical analysis of the plurality of sets of data can be performed to improve the measurement accuracy. In one embodiment, a neural network is used to analyze the data, for example by correlating the different sets of data intelligently. Based on the correlations among the different data sets, the errors or noises in the data can be more readily removed.

The methods can additionally include measuring a set of data without the flow of particles as a reference for calibration. The methods can further include calibrating the apparatus and information obtained from the flow of particles using the reference. This effectively acts as a "negative control". The negative control can be a vacuum or a gas sample known to be substantially free of particles.

The methods can additionally include measuring a set of data using a sample containing a known or pre-determined concentration of particles as a "positive control". The methods can further include calibrating the apparatus using the data obtained using the positive control.

Figure 13:
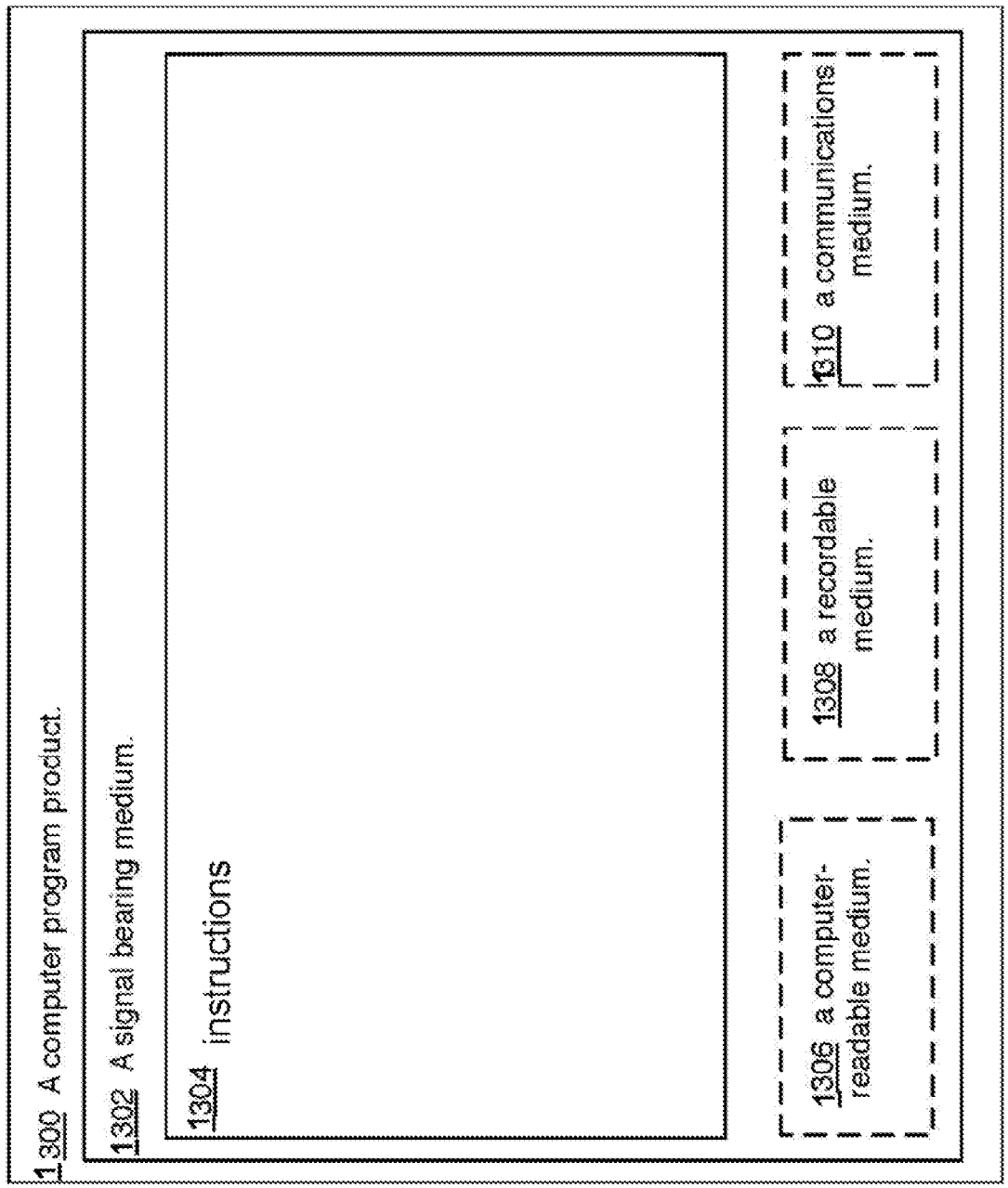
FIG. 13 shows a block diagram of an example computer program.

FIG. 13 is a block diagram illustrating an example computer program product 1300 for use with the apparatus 100 and implementing the methods described above. The computer program product 1300 can include a signal bearing medium 1302, which can include a non-transitory computer readable medium 1306, such as, but not limited to, a hard disk drive, a Compact Disc (CD), a Digital Video Disk (DVD), a digital tape, memory, etc. The computer program product 1300 may also include a recordable medium 1308, such as, but not limited to, memory, read/write (R/W) CDs, R/W DVDs, etc. In some implementations, the signal bearing medium 1302 may encompass a communications medium 1310, such as, but not limited to, a digital and/or an analog communication medium (e.g., a fiber optic cable, a waveguide, a wired communications link, a wireless communication link, etc.). Thus, for example, the computer program product 300 may be conveyed to one or more modules of the apparatus 100 by a radio frequency (RF) signal bearing medium 1302, where the signal bearing medium 1302 is conveyed by a wireless communications medium 1310 (e.g., a wireless communications medium conforming with the IEEE 802.11 standard). Instructions 1304 are stored in the signal bearing medium 1302 to perform the data analysis methods as described above.

EXAMPLES

Example 1

Portable Testing Device

A portable air testing device is prepared. The device includes a display panel that indicates the numeric concentration of nanoparticles in the air, as well as a flashing light and audible alarm indicator for when the nanoparticle concentration exceeds a preselected threshold value. The device includes a memory module that stores the time and concentration of detected nanoparticles.

During measurements, at a time T, one liter of sample is obtained. The sample can include, for example, oxygen, nitrogen, carbon dioxide, water vapor, various inert gases, dust, etc. In this volume, ten small cavities each of 0.1 liter are included. Compositions in the ten small cavities can become completely the same after the sample is fully mixed, and then the ten small cavities are isolated. Data is obtained from each cavity. This configuration can be used to detect whether the instrument is in a stable working state. In addition, the measurement results can be processed. For example, the ten independent small cavities can obtain the same gas samples. If the instrument is stable, then the particle measurements should be the same or similar; if the instrument is unstable, the measurements would be different. Based on the comparison of the measurement results, it can be determined whether the instrument is working in a stable state. On the other hand, using this configuration, by measuring the sample multiple times, statistical analysis can be performed on the measurements, such as taking an average value to reduce measurement errors. In various embodiments, more or fewer than ten cavities may be used. The cavities may be of any suitable size.

Gas transportation into each small cavity can be driven by a piston structure. As data sources are consistent each time, the results of measurement each time would ideally be consistent. In reality, various errors will cause data differences. These data are processed in accordance with the methods described above to reduce errors.

During the process of loading the particles with charges, relevant factors may include: voltage, shape, and size of the charge loader, ambient temperature, moisture, pressure, flow rate, etc.

By convening charged nanoparticles into electrical pulses, a single charged-nanoparticle can be removed from the charged particle receiver (i.e. 140 in FIG. 1) into the charge measuring assembly (i.e., 160 in FIG. 1). The relationship between the charge on the surface of a nanoparticles and its mass/size can be readily obtained.

In one example, a pulse carries 1000 effective charges per millisecond, and a ratio of particles successfully measured to the total particles is 1:10. For the particle feed port with a square opening of 2×2 cm, 1000×10=10,000 particles per millisecond, or 10,000,000 per second can be measured.

During the measurement, if 1000 charge pulses are obtained per millisecond, a threshold is set for the charge such that pulse peak values above or below the threshold are considered invalid. In one example, 40% charge pulse measurement data are screened out as invalid, with the 60% remaining data considered valid. Within the threshold range, the ratio of particles successfully measured can remain the same, e.g., 10%. Thus, the particle feed port 132 with a square opening of 2×2 cm can receive particles to be measured at a rate of 600×10=6,000 per millisecond, or 6,000,000 per second.

If electrical pulses are too crowded, e.g., when particles are excessive, the particle density can be diluted before the measurements. For example, grading chambers can be set through electric valves, wherein each grading chamber will have a volume as big as one tenth of the volume of a chamber of the preceding grade, in which way, one grade will help dilute particles by 10 times; two grades by 100 times; three grades by 1000 times, and so forth.

Example 2

Carbon Nanotube Detector/Collector

In one example, a carbon nanotube detector is provided. The carbon nanotube detector can have a configuration similar to that described above, and be operated in a similar principle.

Example 3

Metallic Nanoparticle Detector/Collector

In one example, a silver nanoparticle detector is provided. The silver nanoparticle detector can have a configuration similar to that described above, and be operated in a similar principle.

Example 4

Semiconductor Nanoparticle Detector/Collector

In one example, a semiconductor nanoparticle detector is provided. The semiconductor nanoparticle detector can have a configuration similar to that described above, and be operated in a similar principle.

Example 5

System with Multiple Sampling Stations

A system can be installed within a semiconductor processing factory, including a single centrally located processor. The processor is connected to an array of twelve separate air sampling apparatus stations via a wireless data network. Each of the stations is located at different locations within the factory, in the factory's various exhaust systems, and outside of the factory building.

The processor monitors the amount of detected particles at each of the stations, and determines rates of change for each of the stations. Both the amount and rate are stored in a data module for archiving and generating reports. The processor includes a display monitor that allows the factory's environmental health and safety (EHS) officer to visually asses the amount and rate of particle production at the factory.

The processor is configured to issue an audible alarm if the amount, rate, or both exceed preprogrammed thresholds. The processor is also configured to issue a notification to the EHS officer by email or mobile phone text message if the thresholds are exceeded at any time of day or on weekends or holidays.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than,"

"less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus for detecting or collecting nanoparticles, the apparatus comprising:
    a charger to electrically charge at least some of the particles;
    a collector to collect at least some of the charged particles; and
    a processor to obtain information indicative of an amount of the detected/collected particles based on measured electrical charges of the charged particles; wherein the collector is configured to measure electrical pulses caused by the collected charged particles, wherein the measured electrical pulses are above a pulse threshold, wherein the collector comprises an electrical pulse detector configured to measure electrical charges based on at least one of a Coulomb repulsion between charged particles, a movement of a charged particle in a magnetic field, a movement of a charged particle in an electric field, or a change in capacitance due to the charged particles.

2. The apparatus of claim 1, further comprising a diluter to reduce a density of the particles being measured.

3. The apparatus of claim 2, wherein the diluter comprises a plurality of grading chambers.

4. The apparatus of claim 3, further comprising a plurality of connectors between two of the plurality of grading chambers, wherein the plurality of connectors each have a different diameter.

5. The apparatus of claim 2, wherein the diluter comprises a sub-chamber and a vacuum valve, wherein the one of the plurality of grading chambers is configured to be evacuated through the vacuum valve, and wherein the sub-chamber is configured to release its content into the one of the plurality of grading chambers to have a diluted content.

6. The apparatus of claim 2, wherein the diluter comprises a plurality of grading channels, each having a different diameter.

7. The apparatus of claim 1, wherein the particles have sizes of about 0.1 nm to about 1000 nm.

8. The apparatus of claim 1, wherein the collector comprises a conductive curved shell configured to have the charged particles move along a surface thereof.

9. The apparatus of claim 8, wherein the charged particles are configured to be dispersed throughout the surface of the conductive curved shell by a Columbic repulsion.

10. The apparatus of claim 1, wherein the collector comprises:
    a conductive mesh to collect the charged particles; and
    at least one of an electric field generator and a magnetic field generator to modify trajectories of the charged particles.

11. A method of detecting or collecting nanoparticles, the method comprising:
    electrically charging at least some of the particles in a flow;
    collecting at least some of the charged particles; and
    obtaining information indicative of an amount of the detected/collected particles based on electrical charges of the collected charged particles; further comprising measuring the electrical charges, wherein the measuring comprises detecting current pulses caused by the collected charged particles, and wherein the detecting is based on at least one of a Coulomb repulsion between charged particles, a movement of charged particles in a magnetic field, movement of charged particles in an electric field, or a change in capacitance due to the charged particles.

12. The method of claim 11, further comprising determining a detection threshold of the current pulses.

13. The method of claim 11, further comprising:
    measuring electrical charges at a plurality of locations; and
    processing measured data from the plurality of locations using a single processor.

14. The method of claim 11, further comprising dispersing the charged particles over a curved conductive shell.

15. The method of claim 14, wherein the curved conductive shell has a semispherical surface.

16. The method of claim 15, wherein the dispersing is through a Coulomb repulsion.

17. The method of claim 11, further comprising diluting a density of the particles in the flow using a plurality of grading chambers.

18. The method of claim 11, further comprising modifying trajectories of the charged particles with at least one of an electric field or a magnetic field.

* * * * *

UNITED STATES PATENT AND TRADEMARK OFFICE
CERTIFICATE OF CORRECTION

PATENT NO. : 8,809,766 B2
APPLICATION NO. : 13/807148
DATED : August 19, 2014
INVENTOR(S) : Ma Page 1 of 1

It is certified that error appears in the above-identified patent and that said Letters Patent is hereby corrected as shown below:

In the Specification,

In Column 13, Line 43, delete "product 300" and insert -- product 1300 --, therefor.

In Column 14, Line 30, delete "convening" and insert -- converting --, therefor.

In Column 14, Line 32, delete "(i.e. 140 in FIG. 1)" and insert -- (i.e., 140 in FIG. 1) --, therefor.

In the Claims,

In Column 18, Line 28, in Claim 11, delete "movement" and insert -- a movement --, therefor.

Signed and Sealed this
Sixteenth Day of December, 2014

Michelle K. Lee
*Deputy Director of the United States Patent and Trademark Office*